United States Patent
Levi et al.

(10) Patent No.: US 9,827,044 B2
(45) Date of Patent: Nov. 28, 2017

(54) COMBINED GALVANIC AND PULSED OPTICAL ENERGY FOR DEPILATION

(71) Applicants: BenZion Levi, Kibbutz Habonim (IL); Moshe Mizrahy, Tel Aviv (IL)

(72) Inventors: BenZion Levi, Kibbutz Habonim (IL); Moshe Mizrahy, Tel Aviv (IL)

(73) Assignee: HOME SKINOVATIONS LTD., Yokneam (IL)

( * ) Notice: Subject to any disclaimer, the term of this patent is extended or adjusted under 35 U.S.C. 154(b) by 742 days.

(21) Appl. No.: 14/071,795

(22) Filed: Nov. 5, 2013

(65) Prior Publication Data

US 2015/0126980 A1    May 7, 2015

(51) Int. Cl.
| | |
|---|---|
| A61B 18/20 | (2006.01) |
| A61B 18/00 | (2006.01) |
| A61B 18/14 | (2006.01) |
| A61B 18/18 | (2006.01) |
| A61N 1/04 | (2006.01) |
| A61N 1/20 | (2006.01) |

(52) U.S. Cl.
CPC ............ *A61B 18/203* (2013.01); *A61B 18/14* (2013.01); *A61B 2018/00476* (2013.01); *A61B 2018/00642* (2013.01); *A61B 2018/00708* (2013.01); *A61B 2018/00809* (2013.01); *A61B 2018/00815* (2013.01); *A61B 2018/00821* (2013.01); *A61B 2018/00994* (2013.01); *A61B 2018/1807* (2013.01); *A61N 1/0412* (2013.01); *A61N 1/205* (2013.01)

(58) Field of Classification Search
CPC .................. A61B 18/14; A61B 18/203; A61B 2018/00476; A61B 2018/00642; A61B 2018/00708; A61B 2018/00809; A61B 2018/00815; A61B 2018/00821; A61B 2018/00994; A61B 2018/001807; A61N 1/205; A61N 1/00412
USPC ............................................................ 606/9
See application file for complete search history.

(56) References Cited

U.S. PATENT DOCUMENTS

| | | | |
|---|---|---|---|
| 4,813,412 A | 3/1989 | Yamazaki | |
| 6,090,101 A * | 7/2000 | Quon | A61B 18/203 606/9 |
| 6,702,808 B1 * | 3/2004 | Kreindel | A61B 18/14 128/898 |
| 8,606,366 B2 * | 12/2013 | Flyash | A61B 18/203 607/98 |
| 8,876,809 B2 * | 11/2014 | Eckhouse | B26B 19/46 606/9 |

(Continued)

FOREIGN PATENT DOCUMENTS

| | | |
|---|---|---|
| WO | 98/58592 | 12/1998 |
| WO | 02/26147 | 4/2002 |

(Continued)

OTHER PUBLICATIONS

PCT Search Report, PCT/US2014/063762, Feb. 13, 2015.

*Primary Examiner* — Gary Jackson
*Assistant Examiner* — Boniface N Nganga
(74) *Attorney, Agent, or Firm* — Dekel Patent Ltd.; David Klein

(57) ABSTRACT

A method for photothermolysis that includes applying galvanic current energy to skin at an area of a hair follicle and applying pulsed optical energy to the skin at the area of the hair follicle at an energy level and duration so as to cause thermal destruction of a hair papilla.

7 Claims, 1 Drawing Sheet

(56) References Cited

U.S. PATENT DOCUMENTS

| | | | | |
|---|---|---|---|---|
| 8,882,753 | B2 * | 11/2014 | Mehta | A61B 18/14 128/898 |
| 2005/0045189 | A1 * | 3/2005 | Jay | A61B 5/0059 128/898 |
| 2005/0215987 | A1 * | 9/2005 | Slatkine | A61B 18/203 606/9 |
| 2006/0173518 | A1 * | 8/2006 | Kreindel | A61B 18/14 607/101 |
| 2008/0125835 | A1 * | 5/2008 | Laurent | A61N 5/0617 607/89 |
| 2008/0319507 | A1 * | 12/2008 | Myers | A61B 18/203 607/50 |
| 2009/0149796 | A1 * | 6/2009 | Jones | A61B 18/203 604/20 |
| 2009/0204109 | A1 * | 8/2009 | Grove | A61B 18/203 606/9 |
| 2010/0198199 | A1 * | 8/2010 | Kreindel | A61B 18/14 606/9 |
| 2010/0274329 | A1 * | 10/2010 | Bradley | A61N 5/0616 607/90 |
| 2012/0090181 | A1 * | 4/2012 | Broekhuizen | A45D 26/0023 30/123 |
| 2012/0109114 | A1 * | 5/2012 | Waldman | A61B 18/203 606/3 |
| 2012/0165800 | A1 * | 6/2012 | Keeney | A61B 18/203 606/9 |
| 2012/0197135 | A1 * | 8/2012 | Slatkine | A61B 18/203 600/476 |
| 2012/0271289 | A1 * | 10/2012 | Eckhouse | A45D 26/0028 606/9 |
| 2013/0030421 | A1 * | 1/2013 | Gomez De Diego | A61B 18/203 606/3 |
| 2013/0144280 | A1 * | 6/2013 | Eckhouse | A45D 26/00 606/9 |
| 2014/0081250 | A1 * | 3/2014 | Eckhouse | A45D 26/00 606/9 |

FOREIGN PATENT DOCUMENTS

| | | | | |
|---|---|---|---|---|
| WO | WO 2009109885 A2 * | 9/2009 | | A61B 18/203 |
| WO | 2012/171010 | 12/2012 | | |

* cited by examiner

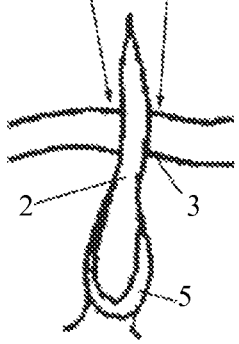
FIG. 1
FIG. 2
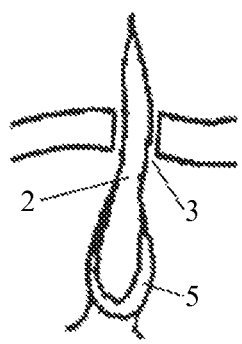
FIG. 3
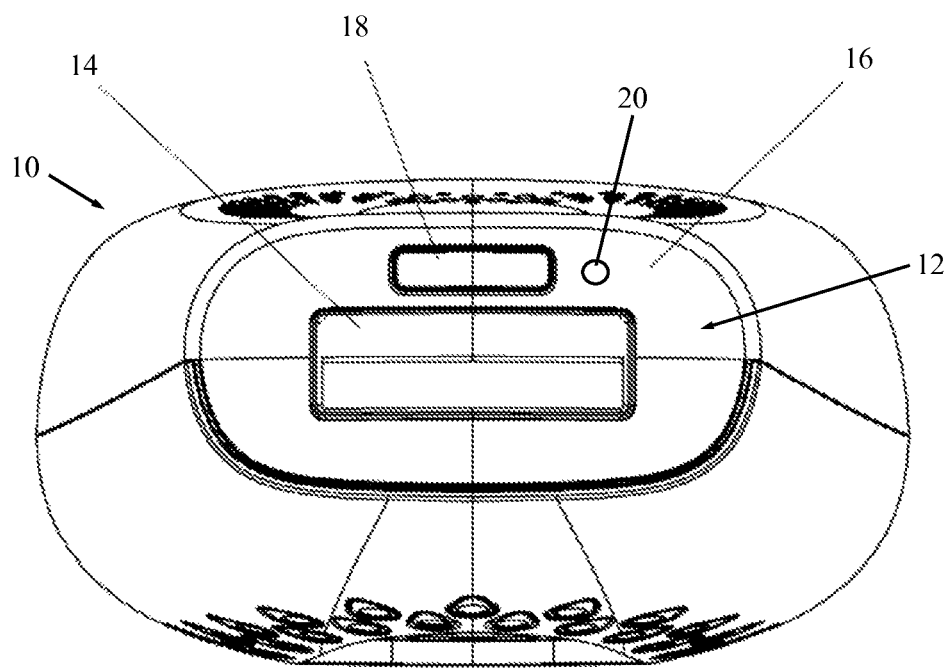
FIG. 4

COMBINED GALVANIC AND PULSED OPTICAL ENERGY FOR DEPILATION

FIELD OF THE INVENTION

The present invention relates to depilation (hair removal) by photothermolysis, and particularly a depilatory device that combines galvanic current energy with intense pulsed light (IPL) and/or pulsed laser energy.

BACKGROUND OF THE INVENTION

As is well known in the art of depilation, light energy can be used to destroy the hair follicle, but must be of sufficient magnitude and frequency. For example, although light emitting diodes (LEDs) deliver optical energy, the energy is continuous wave with low magnitude and is insufficient to destroy the hair follicle. Instead, LED is used for skin rejuvenation. Hair removal is done with intense pulsed light (IPL) or pulsed laser energy. The optical energy currently used in the prior art to destroy hair follicles is usually delivered in very short pulses, e.g., tens of milliseconds, so that the energy can penetrate through the skin to the follicle.

Light energy that causes thermal destruction of the hair shaft and follicle is in the range of wavelengths that are specifically absorbed by the pigment melanin found in the hair follicle, also referred to as selective photothermolysis. However, a known problem is that the epidermis through which the light energy must penetrate is rich in melanin and therefore absorbs a major portion of the energy, resulting in inadequate heating of the hair follicles as well as damage to the epidermis. Using higher energy levels in order to generate sufficient heating of the hair follicles can cause charring and hyper-pigmentation. It is known that high energy used on dark skin with either IPL or lasers can create burns.

Another problem with selective photothermolysis is that the wavelength may be insufficient for penetration deep enough to reach the target due to tissue scattering which depends on wavelength. Various techniques have been used or proposed to assist in improving the efficiency of the process. These techniques include cooling of the treated area before or during application of the light energy, or focusing techniques aimed at focusing the optical energy at a specific depth under the skin surface, so as to increase the energy fluence at that depth.

SUMMARY OF THE INVENTION

The present invention seeks to provide improved methods and a device for depilation by photothermolysis that solve the above-mentioned problems of the prior art in a novel way.

In the present invention, the depilatory device combines continuous galvanic energy with pulsed optical energy (either IPL or laser). Without being bound by any theory, the galvanic energy opens the pores around the hair follicle to increase exposure of the hair follicle for the optical pulsed energy. The galvanic energy works as preparation for the optical pulsed energy. The galvanic current is a continuous wave but is not at a level capable of destroying the follicle.

Thus, the galvanic energy used in the present invention is not to be confused with galvanic energy used in the prior art for depilation. In prior art galvanic depilation, direct current is generally passed through a needle to produce sodium hydroxide in the follicle, which destroys the hair papilla. In contrast, in the present invention, the galvanic energy is at a very different level and opens the pores and prepares the treated area for penetration of the pulsed energy. In addition, the galvanic micro-current may produce a minor heating effect of the hair papilla or follicle, but at a non-destructive level. Galvanic current/micro-current in the prior art is used to help penetration of a cosmeceutical into the skin. Galvanic current/micro-current has not been used for hair removal in the prior art. In the following description and claims, the terms galvanic current, galvanic energy and micro-current are used interchangeably.

BRIEF DESCRIPTION OF THE DRAWINGS

These and additional constructional features and advantages of the invention will be more readily understood in the light of the ensuing description of embodiments thereof, given by way of example only, with reference to the accompanying drawings wherein:

FIGS. 1-3 are simplified pictorial illustrations of a method for depilation by photothermolysis, using a combination of galvanic energy and pulsed optical energy, in accordance with a non-limiting embodiment of the present invention; and FIG. 4 is a simplified pictorial illustration of a device for implementing the depilation method of FIGS. 1-3, in accordance with a non-limiting embodiment of the present invention.

DETAILED DESCRIPTION OF EMBODIMENTS

Reference is now made to FIGS. 1-3, which illustrate a method for depilation by photothermolysis, using a combination of galvanic energy and pulsed optical energy, in accordance with a non-limiting embodiment of the present invention.

In FIG. 1, galvanic current energy is applied to skin at the area of a hair follicle 2. The galvanic current is generated by a galvanic micro-current unit 4. The galvanic current is a continuous wave or pulsed, but is not at a level capable of destroying the hair papilla 5. Without limitation, the galvanic current is in the range of 10-500 microamperes. It is believed the galvanic energy opens the pore 3 around the hair follicle 2 to increase exposure of the hair follicle 2 for subsequent application of pulsed optical energy. FIG. 2 illustrates the hair follicle 2 with the increased pore 3.

In FIG. 3, pulsed optical energy is applied to the skin at the area of hair follicle 2 so as to cause thermal destruction of the hair papilla 5. The pulsed optical energy is generated by a pulsed optical energy source 6, which may emit intense pulsed light (IPL) and/or pulsed laser energy. Without limitation, operating parameters may be as follows:

Optical energy—either IPL or laser—in a range of 2.5-40 Joules per $cm^2$

Pulse duration of the optical energy—0.5-30 milliseconds

Spectrum for the laser—wavelength in a range of 700-1100 nm

Spectrum for the IPL—in a range of 450 nm-1200 nm

Reference is now made to FIG. 4, which illustrates a depilatory device 10 for implementing the depilation method of FIGS. 1-3, in accordance with a non-limiting embodiment of the present invention.

Device 10 includes a skin interface element 12. The galvanic micro-current unit and the pulsed optical energy source (not shown in FIG. 4) may be mounted on a suitable substrate or printed circuit board (not shown in FIG. 4) behind skin interface element 12. Skin interface element 12 includes a pulsed optical energy skin interface portion 14, which is preferably light transparent and may be made, for example, from polycarbonate or other transparent material. The pulsed optical energy from the pulsed optical energy source is applied to the skin through the pulsed optical energy skin interface portion 14. Skin interface element 12 also includes a conductive surface 16, which provides the galvanic micro-current connection to the skin. Device 10 may also include a skin color sensor 18, located behind a window formed in skin interface element 12. Skin color sensor 18 is used to measure the skin color in order to determine if optical energy can be applied on the skin and/or the level of energy to be applied. As is known in the art, skin color sensor may include, without limitation, a light source and a photodiode (not shown). By shining the light source on the surface of the skin and reading its reflection with the photodiode, the skin color can be determined Skin interface element 12 may be applied directly to the skin or alternatively through conducting media, such as gel, cream and the like.

A temperature sensor 20 may be provided, such as in a portion of skin interface element 12, for detecting the skin temperature. Without limitation, temperature sensor 20 may be an infrared (IR) temperature element, a thermistor (positive or negative coefficient), thermo-transistor, thermo-couple, and others. Temperature sensor 20 may operate in a control loop with control circuitry (not shown) to control or cut off energy in accordance with the feedback temperature sensed.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A method for depilation or hair removal by photothermolysis that combines galvanic current energy and pulsed optical energy, the method comprising:

applying galvanic current energy to skin at an area of a hair follicle at a level incapable of destroying hair papilla, to open a pore around the hair follicle;

and applying pulsed optical energy to the skin at the area of the hair follicle with the open pore at an energy level and duration so as to cause thermal destruction of a hair papilla.

2. The method of claim 1, wherein the galvanic current energy is continuous wave energy.

3. The method of claim 1, wherein the open pore increases exposure of the hair follicle the optical energy.

4. The method according to claim 1, wherein the pulsed optical energy comprises at least one of intense pulsed light (IPL) and pulsed laser energy.

5. The method according to claim 1, wherein the pulsed optical energy is in a range of 2.5-40 $J/cm^2$ and has a pulse duration of 0.5-30 milliseconds.

6. The method according to claim 1, wherein the pulsed optical energy comprises laser energy that has a wavelength in a range of 700-1100 nm.

7. The method according to claim 1, wherein the pulsed optical energy comprises IPL that has a wavelength in a range of 450 nm-1200 nm.

* * * * *